(12) United States Patent
Gerhold et al.

(10) Patent No.: US 10,214,702 B2
(45) Date of Patent: Feb. 26, 2019

(54) BIOGAS BLENDING AND VERIFICATION SYSTEMS AND METHODS

(71) Applicant: Mustang Sampling LLC, Ravenswood, WV (US)

(72) Inventors: Walter F. Gerhold, Dallas, NC (US); Austin Hill, Troutman, NC (US)

(73) Assignee: Mustang Sampling LLC, Ravenswood, WV (US)

( * ) Notice: Subject to any disclaimer, the term of this patent is extended or adjusted under 35 U.S.C. 154(b) by 0 days.

(21) Appl. No.: 15/817,710

(22) Filed: Nov. 20, 2017

(65) Prior Publication Data

US 2018/0155649 A1 Jun. 7, 2018

Related U.S. Application Data

(60) Provisional application No. 62/429,409, filed on Dec. 2, 2016.

(51) Int. Cl.
| | |
|---|---|
| *C10L 3/10* | (2006.01) |
| *B01F 3/02* | (2006.01) |
| *B01F 5/04* | (2006.01) |
| *B01F 15/00* | (2006.01) |
| *C10L 3/08* | (2006.01) |
| *G05D 21/02* | (2006.01) |

(52) U.S. Cl.
CPC ............... *C10L 3/10* (2013.01); *B01F 3/028* (2013.01); *B01F 5/0403* (2013.01); *B01F 15/00149* (2013.01); *B01F 15/00253* (2013.01); *C10L 3/08* (2013.01); *G05D 21/02* (2013.01); *C10L 2290/24* (2013.01); *C10L 2290/58* (2013.01); *C10L 2290/60* (2013.01)

(58) Field of Classification Search
CPC combination set(s) only.
See application file for complete search history.

(56) References Cited

U.S. PATENT DOCUMENTS

| 3,702,619 A | 11/1972 | Son |
| 3,948,281 A * | 4/1976 | Strain ............... B01F 3/026 137/3 |
| 6,684,644 B2 | 2/2004 | Mittricker et al. |

(Continued)

FOREIGN PATENT DOCUMENTS

CN 102154046 B 7/2013

OTHER PUBLICATIONS

Aether DBS, Biogas Blending System, Bio-Solids Processing Facility, California, http://www.aetherdbs.com/portfolio_item/biogas-blending-system-bio-solids-processing-facility-california, p. 1.

(Continued)

*Primary Examiner* — Kaity V Chandler
(74) *Attorney, Agent, or Firm* — Cahn & Samuels, LLP

(57) ABSTRACT

A biogas blending and energy content verification system and method for controlled enhancement of a biogas feedstock stream energy content profile by selective sampling and analysis of the biogas feedstock stream and controlled injection of a refined gas of a known, higher energy content into the biogas feedstock stream to produce a blended biogas having an augmented energy content profile meeting or exceeding a pre-established minimum to meet end user requirements.

17 Claims, 3 Drawing Sheets

(56) References Cited

U.S. PATENT DOCUMENTS

| | | | |
|---|---|---|---|
| 7,063,097 B2 * | 6/2006 | Arno | G01N 21/3504 |
| | | | 137/3 |
| 7,497,191 B2 * | 3/2009 | Fulton | G06Q 30/0225 |
| | | | 123/3 |
| 8,158,378 B2 | 4/2012 | Mitariten | |
| 2013/0239470 A1 * | 9/2013 | Buchanan | C10L 1/06 |
| | | | 44/451 |
| 2014/0043932 A1 | 2/2014 | Russell et al. | |
| 2014/0311213 A1 | 10/2014 | Thompson et al. | |
| 2015/0000426 A1 | 1/2015 | Rolston et al. | |
| 2015/0047712 A1 | 2/2015 | Little, III et al. | |
| 2015/0362468 A1 | 12/2015 | Gerhold | |

OTHER PUBLICATIONS

Preferred Utilities MFG Corporation, Blending Skids, http://www.preferred-mfg.com/products/wn/Blending-Skids, pp. 1-2.

E3 Fuel Blending Glass Engine Control System: Combines high-quality natural gas with low-quality bio-gas fuels, http://www.woodard.com/gase3fuelblending.aspx, pp. 1-2.

English translation of CN 102154046 B, dated Jul. 13, 2013.

International Search Report and Written Opinion, PCT/US17/63846, dated Mar. 9, 2018.

* cited by examiner

BIOGAS BLENDING AND VERIFICATION SYSTEMS AND METHODS

FIELD OF INVENTION

This invention relates to a biogas blending and verification system adapted for use with a refinement system for processing biogas sources. A biogas feedstock stream from a first source, such as a multi-stage refinement system, is sampled for analysis of composition and combustion energy profile. When the combustion energy content profile is detected to fall under a pre-set minimum, a control unit actuates a valve disposed in a refined gas stream, where the refined gas possesses a known energy content to inject the refined gas into the biogas feedstock stream to yield a blended biogas. The blended biogas is then sampled to confirm that it achieves a predetermined energy content threshold that meets requirements and/or engine specifications.

BACKGROUND OF THE INVENTION

Biogas, also referred to as bio-methane, swamp gas, landfill gas, and digester gas, is the product of anaerobic digestion, e.g., the decomposition of waste material without the presence of oxygen which yields predominantly methane and carbon dioxide. After proper processing to appropriate purity, captured biogas is usable as a green/renewable fuel or fuel for natural gas-powered vehicles/engines. One such system for multi-stage biogas treatment is detailed in U.S. Pat. No. 9,535,045, which describes a system to process biogas. The content of that patent is incorporated herein by reference.

Several generation and collection sources of biogas exist across a wide range of disciplines, i.e., waste water treatment, solid waste/land fill disposal and management, food processing plants, and the agricultural industry, including processing farm animal waste.

Before it can be used effectively as a fuel source, however, biogas must be processed. Such processing requires removal and/or minimization of typical impurities found in the biogas output stream. The cleaning begins with particulate removal, followed by removal of water, and, when the desired end product is intended to provide a high quality gas stream, $H_2S$, sulfur species, siloxanes, $CO_2$, digestion generated VOCs (Volatile Organic Chemicals) and oxygen. Subject to required purity/energy content standards, the resulting cleaned gas may be utilized as CNG (Compressed Natural Gas) for powering vehicles.

The purity requirements for use of processed biogas as Natural Gas Vehicle (NGV) fuel or compressed natural gas (CNG) are established by standards such as ISO 15404-2006. In addition to the above-mentioned scrubbing, that standard calls for the removal of all moisture for the gas to be compressed at high pressures, e.g., 6,000 psig. The success of such processing must again be confirmed through sample takeoff and analysis.

Particularly in the context of CNG, a need exists for a system and method assuring maintenance of a pre-established energy content from an obtained biogas stream and providing augmentation by blending of a refined gas with the biogas stream of when the content falls below the pre-established minimum combustion energy profile threshold.

SUMMARY OF THE INVENTION

It is an object of the present invention to provide systems and methods for detecting, augmenting, and maintaining established energy content of a biogas stream at a pre-established minimum combustion energy threshold.

Another object of the invention is to provide a novel system and method for selectively introducing and blending a refined gas of known energy content with a biogas feedstock stream to generate a blended biogas output satisfying a preset energy content threshold.

A further object of the invention is to generate a blended biogas output that conforms with known energy content requirements.

Still a further object of the invention is to provide a system and method for blending biogas to achieve a threshold combustion energy profile relying in part, on detecting, monitoring and regulating the respective flow rates of a refined control gas and a biogas feedstock stream.

Yet a further object of the invention is to provide a gas blending system for automatically monitoring the energy content level of a processed biogas and increasing the energy content thereof with the addition of a refined gas upon detection of energy content falling below a select threshold.

These and other objects are satisfied by a gas blending system comprising: a biogas feedstock source providing a biogas feedstock stream having a first energy content; a first sample take-off probe for sample take-off from said biogas feedstock stream for energy content analysis; an analyzer for energy content analysis and generating data signals representative thereof; a control unit for receiving said energy content analysis data signal and transmitting a control signal responsive thereto; a refined gas source in selective fluid communication with said biogas feedstock stream and disposed downstream of said first sample take-off probe, the refined gas source selectively providing a refined gas having a known energy content exceeding that first energy content; a valve in signal communication with said control unit for responding to the transmitted signal, said valve for controlling refined gas flow from said refined gas source, said valve being actuatable between a first open position and a second closed position, where said valve when in said first open position selectively introduces said refined gas into the biogas feedstock stream to generate a blended biogas stream upon detection of said first energy content falling below a preset minimum; a second sample take-off probe for sample take-off from said blended biogas stream, said second take-off probe being disposed downstream of said refined gas input source, for energy content analysis and energy content verification of said blended biogas stream as meeting or exceeding said preset threshold; and an output of said blended biogas stream.

The foregoing and still other objects of the invention are satisfied by a method of blending a biogas feedstock stream from a first source having a first energy content with a refined gas from a second refined gas source having a known energy content higher than the first energy content to provide a blended biogas having a third energy content in a select range using a gas blending system including a system interface and a control unit in signal communication with an actuatable valve disposed a refined gas source, comprising the steps of: a) extracting a sample from the biogas feedstock stream; b) conditioning the extracted sample for analysis by an energy content analyzer and generating data corresponding to the biogas feedstock stream energy content; c) determining if the biogas stream possesses an energy content less than a pre-established minimum; d) generating a control signal by the control unit when the first energy content is detected to fall below the pre-established minimum and communicating the control signal to said actuatable valve for injection of a refined gas into the biogas feedstock stream to form the blended biogas; e) extracting a sample of the blended biogas and analyzing the energy content thereof to verify the third energy content exceeds the pre-established minimum; and outputting the blended biogas.

The invention provides a biogas energy content and blending system adapted for monitoring characteristics of a biogas feedstock stream from a first source and for controlling introduction of a refined gas from a refined gas source, such as natural gas or propane with a known, elevated energy content value, to yield a blended biogas with augmented energy content satisfying the requirements of specific standards and/or established CNG engine warranty protocols.

The gas blending system is readily employable in combination with a multi-stage system providing a biogas feedstock stream as described in the aforementioned patent U.S. Pat. No. 9,535,045. The refined gas stream, possessing a combustion energy profile suitable for increasing the overall energy content of the biogas feedstock stream, is selectively introduced into the biogas feedstock stream.

In an exemplary embodiment, the gas blending system includes at least a first and second sample takeoff probe disposed in the biogas feedstock and blended biogas streams at positions before and after the gas blending pipe section, respectively. The first sample takeoff probe is used to extract an unblended sample from the biogas feedstock stream, which is directly communicated to an appropriate analyzer, e.g., a gas chromatograph (GC). When the combustion energy level of the unblended biogas is detected as falling below a preselected minimum, a signal from a control unit is transmitted to open an actuatable valve (e.g., electromechanical, solenoid valve, etc.) disposed between the refined gas source and the biogas feedstock stream. Upon actuation, the valve switches from a closed to a modulated open or fully open position to introduce refined gas into the biogas feedstock stream to create a blended biogas with a higher overall energy content. The second sample takeoff probe located downstream extracts a sample of blended biogas downstream from the refined gas injection which is passed to an analyzer for compositional/energy content evaluation. Data obtained from the blended biogas sample is transmitted from the analyzer to a control unit for verification of achieving the necessary enhancement of the energy content to satisfy the quality requirements of the end-user. The data also is employed to control the flow rate of the refined gas injected into the biogas feedstock stream to minimize waste resulting from introducing excessive refined gas into the biogas feedstock stream.

Introduction of the refined gas into the biogas feedstock stream is not necessarily continuous. When the compositional/energy content of the unblended biogas feedstock sample from the first take-off is determined to be sufficient, there is no need to augment the energy profile of the biogas feedstock steam. In such a case, the control unit maintains the actuatable valve in the closed position and allows the biogas feedstock stream to pass to the system output without refined gas blending.

The inventive gas blending method and system may also incorporate flow sensors for detecting and measuring the flow of the unblended biogas feedstock stream and the flow of the refined gas stream providing signal transmission to a control unit. The resulting flow rate determinations provide additional data to supplement determinations of energy content analysis of the respective biogas stream and refined gas input. Such flow rate measurements may provide enhanced accuracy as a redundant alternative measurement confirming that a proper blend has been obtained and may signal the need to increase or decrease the quantity of refined gas being injected into the biogas feedstock stream. If the processed flow rate data a need to increase or reduce refined gas flow volume, the control unit sends a signal indicating the need to modulate refined gas flow through the valve.

The inventive gas blending method and system may also incorporate a refined gas impingement tube adjunct at the point of injection to promote more uniform cross-sectional introduction of the refined gas into the biogas feedstock stream.

The terminology used herein is for the purpose of describing particular embodiments only and is not intended to be limiting of the invention.

As used herein, the singular forms, "a", "an" and "the" are intended to include the plural forms as well, unless the context clearly indicates otherwise. It will be further understood that the root terms "include" and/or "have", when used in this specification, specify the presence of stated features, steps, operations, elements, and/or components, but do not preclude the presence or addition of at least one other feature, step, operation, element, component, and/or groups thereof.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus.

For definitional purposes and as used herein "connected" includes physical, whether direct or indirect, affixed or adjustably mounted. Thus, unless specified, "connected" is intended to embrace any operationally functional connection.

In this detailed description, references to "one embodiment", "an embodiment", or "in embodiments" mean that the feature being referred to is included in at least one embodiment of the invention. Moreover, separate references to "one embodiment", "an embodiment", or "embodiments" do not necessarily refer to the same embodiment; however, neither are such embodiments mutually exclusive, unless so stated, and except as will be readily apparent to those skilled in the art. Thus, the invention can include any variety of combinations and/or integrations of the embodiments described herein.

As used herein, and unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

As used herein "substantially," "generally," and other words of degree are relative modifiers intended to indicate permissible variation from the characteristic so modified. It is not intended to be limited to the absolute value or characteristic which it modifies but rather possessing more of the physical or functional characteristic than its opposite, and preferably, approaching or approximating such a physical or functional characteristic.

In the following description, reference is made to the accompanying drawings, which are shown by way of illustration to the specific embodiments in which the invention may be practiced. The following illustrated embodiments are described in sufficient detail to enable those skilled in the art to practice the invention. It is to be understood that other embodiments may be utilized and that structural changes based on presently known structural and/or functional equivalents may be made without departing from the scope of the invention.

DETAILED DESCRIPTION OF THE DRAWINGS

Figure 1:
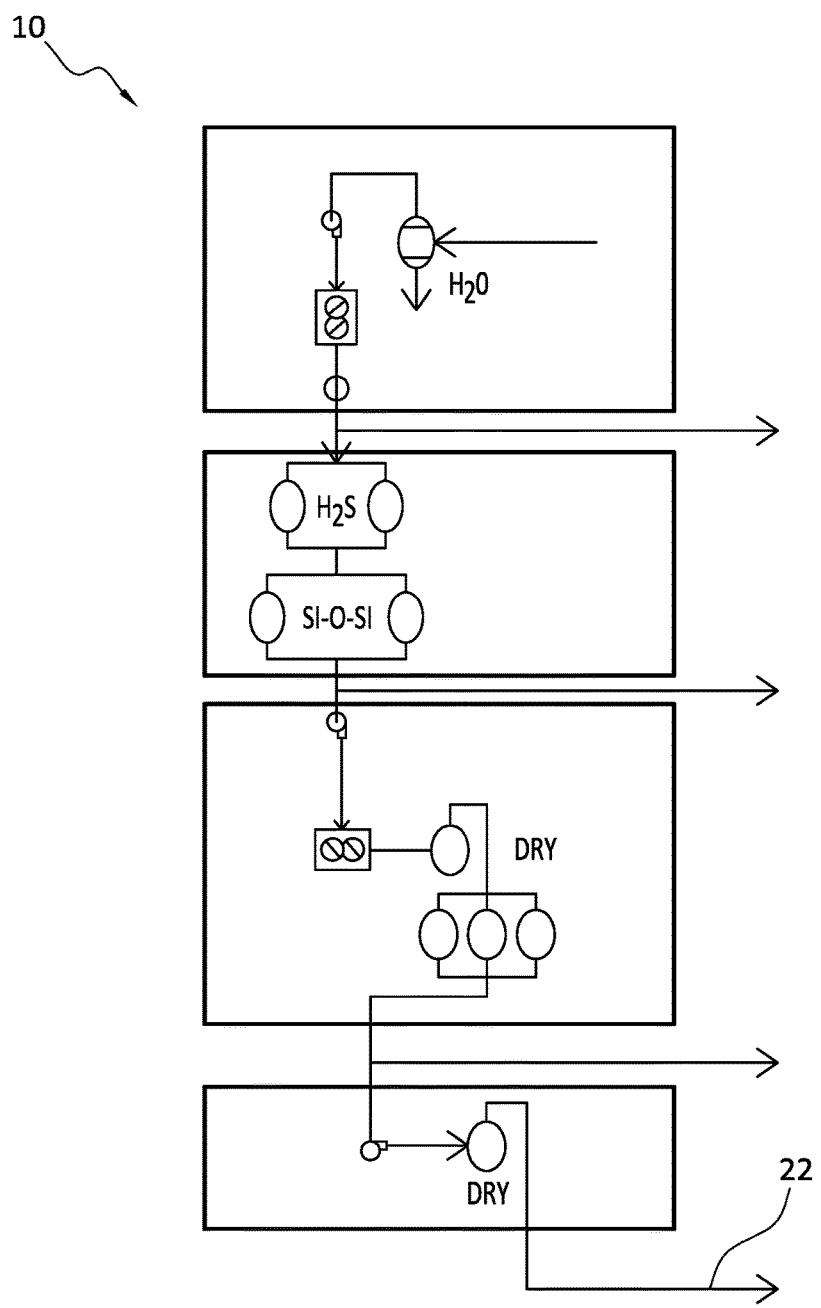
FIG. 1 illustrates an example of a prior art multi-stage biogas refinement system flow diagram.

FIG. 1 illustrates a prior art, multi-stage biogas refinement system 10 having four different levels of processing. The disclosed multi-stage refinement system 10 is of a type comprising the subject matter of U.S. Pat. No. 9,535,045, the content of which is herein incorporated by reference in its entirety.

Figure 2:
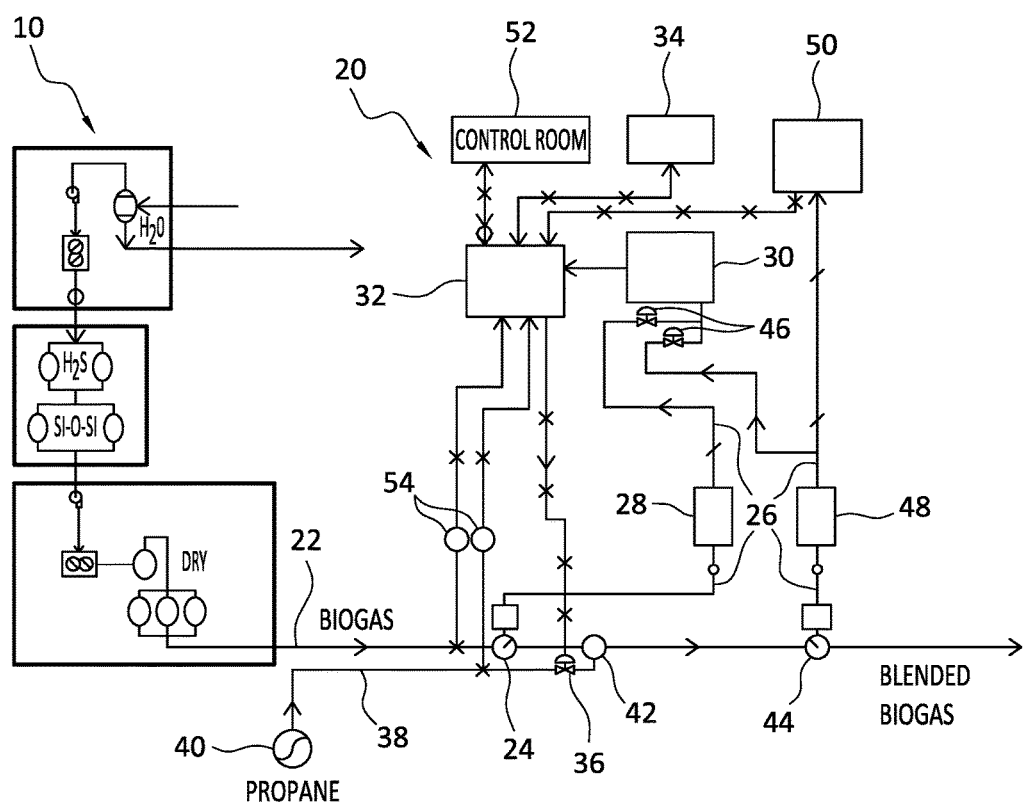
FIG. 2 illustrates a process flow diagram for a biogas blending and verification system according to an embodiment of the invention.

FIG. 2 illustrates a gas blending system 20 that is the focus of the present invention. The gas blending system 20 is connected at the refined biogas output level 22 of the multi-stage refinement system 10. Scrubbed biogas having a value of approximately 900-950 BTU is removed from the multi-level refinement system 10 and a biogas feedstock stream is communicated through the biogas feedstock conduit 22, passing a first sample takeoff probe 24 in which the unblended biogas feedstock stream is sampled. The biogas feedstock sample is communicated to a first gas sample conditioning unit 28 to insure proper pressure and temperature during the pressure drop required to pass the sample from the take-off to the analyzer at a non-damaging pressure. An example of one such conditioning unit is a Mustang Model 2 sample condition system and like that described and disclosed in U.S. Pat. No. 7,484,404 and its progeny, the content of which is incorporated herein by reference.

In embodiments having an analyzer 30 remotely spaced from the conditioner, the conditioned biogas sample preferably is communicated through thermally stabilized heat traced tubing 26 from the sample conditioning unit 28 to the analyzer 30 in a sample analysis array. Heat trace power provision of this type is described in U.S. Pat. No. 7,162,933, the content of which is incorporated herein by reference. The analyzer 30 preferably has a multi-input capability such as a ROSEMOUNT 570 chromatograph available from Emerson, capable of measuring the BTU value of multiple gas sample streams.

Following sample analysis by the analyzer 30, data is communicated to a control unit 32, such as a PLC/PID controller which in the illustrated embodiment is a WATLOW controller, and is displayed using a system interface 34 having a processor, a touch screen, and an input device. The system interface 34 is preferably associated with a laptop or other display coupled thereto. Based on the data processed by the control unit 32 and the energy content requirements of the end-user, an actuatable valve 36, such as a solenoid valve, in the refined gas conduit 38 is opened by the control unit 32 to facilitate blending of a volume of refined gas from a refined gas source 40 having a known energy content with the biogas stream in the biogas feedstock conduit 22. The refined gas source 40 is preferably a source such as propane or highly-refined natural gas with a high, known energy content level, that will increase the overall energy content of the biogas in the biogas feedstock stream when blended therewith.

The valve 36 is in signal communication with the control unit 32, e.g., wireless or electrical communication, and cooperates to regulate the flow of refined gas through the refined gas conduit 38. When data from the biogas stream sample establishes that pre-existing compositional characteristics in the sample's unblended state are sufficient to satisfy desired quality requirements, there is no need to introduce the refined gas to the biogas feedstock stream. In such an event, the control unit 32 ensures the actuatable valve 36 is actuated to/remains at a closed position, thereby allowing the unblended biogas to flow downstream for custody transfer or other use. However, more commonly, the biogas feedstock stream will possess an energy content level below the prescribed minimum threshold. In such a case, energy content augmentation is necessary.

To achieve such augmentation, the disclosed embodiment of FIG. 2 features a junction 42 disposed at the intersection of the biogas feedstock conduit 22 and the refined gas conduit 38. The refined gas stream flows through the refined gas conduit 38 and is injected into the biogas feedstock stream at a blending pipe junction 42.

The resulting blended biogas stream moves downstream from the gas blending pipe junction 42 past a second in-line sample takeoff probe 44 to an output. At the take-off, a sample is extracted, optionally passed through a sample conditioner unit 48, and passed to an analyzer. If the system includes a second analyzer 50, the sample may be passed directly to it or, as illustrated, through a manifold or analyzer distribution panel 45 allowing for controlled serial distribution of the blended biogas sample to the same analyzer 30 employed for the analysis of the original biogas feedstock stream. If directed to analyzer 30, the sample communication conduit includes a solenoid actuated valve 46 linked to the control unit to insure isolation of that line from any input from the unblended sample passing to the analyzer from take-off probe 24 as should the unblended sample conduit include an isolation valve 46 to prevent undesired admixing of the streams to the analyzer 30 and to provide operational control of blended and unblended gas samples input to analyzer 30 for gas property analysis of multiple sample streams.

Following communication of sample take-off to the analyzer 30 and, in the case of the blended biogas stream to the second analyzer 50, the energy content analysis data is communicated to the control unit 32. When the gas combustion profile of the unblended biogas feedstock stream satisfies pre-established minimum requirements of an end-user, the valve 36 remains closed. However, when the minimum is breached, then the control unit 32 sends an actuating signal to open the valve 36 to introduce refined gas to the biogas feedstock stream and generate a blended biogas. The blended biogas is then subject to sample take-off, either periodically or continuously, and analysis to assess the energy content of the blended biogas assuring that the minimum energy content requirements have been and continue to be satisfied. Upon detection of the biogas feedstock stream possessing sufficient energy content, then the control unit 32 de-actuates the solenoid valve to prevent introduction of the refined gas into the biogas feedstock stream Using service programs, such as SOFTVIEW, associated with the processor/system interface 34, the operator is able to maintain a flow ratio suitable for providing a desirable biogas combustion profile. In embodiments, the WATLOW controller switches to flow control automatically when it detects signal input failure from the GC unit. This results in increased efficiency and reduced downtime, thereby increasing productivity and profit. The operator is able to override the automatic flow control by optionally switching the system controller 32 to a manual mode.

Figure 3:
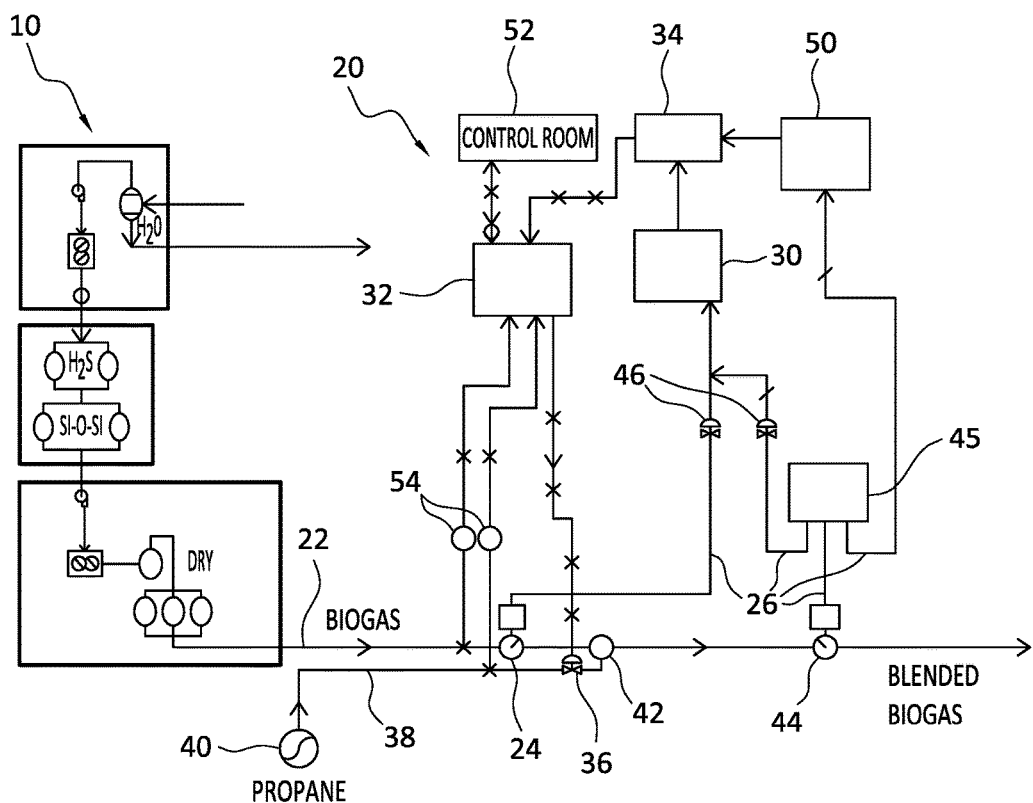
FIG. 3 illustrates a process flow diagram for a biogas blending and verification system according to a second embodiment of the invention.

FIG. 3 illustrates a second embodiment of the biogas blending system 20 according to the invention where the analyzer 30 and the second analyzer 50 transmit data directly to the system interface 34 and the system interface 34 establishes signal communication with the control unit 32. The biogas blending system 20 further includes a modular distribution panel 45 such as a MMADP available from Mustang Sampling of Ravenswood, W. Va., to selectively isolate and control pressure of the blended biogas sample respectively communicated to the analyzers (30, 50).

The embodiments may also include a system operator control room 52 providing the operator with immediate access to measurements of energy content results from the analyzer(s) and the flow rate data generated by detectors 54. As illustrated, the control room 52 is connected to the control unit 32 and may provide optional operator manual override controls for any of the electrically actuated solenoid valves in the system and thereby control the output of the biogas feedstock stream and refined gas injection therein. The control room 52 may also include a data recording capability for archiving and production of energy audit documents.

In an enhanced embodiment promoting enhanced homogenous blending of the two streams at the junction 42, the refined gas may be introduced into the biogas stream through an impingement tube projecting into the biogas feedstock stream. Providing a series of radially oriented, axially spaced holes, at predetermined intervals along the impingement tube length promotes more uniform admixing of refined gas with the biogas feedstock streams and, therefore, a more homogeneous blended product.

In a further modification contemplated to fall within the spirit and scope of the invention, a system incorporating a two-stream chromatograph such as that illustrated in FIG. 2 includes a flow control loop providing either flow-rate measurement based on redundant indication of effective refined gas injection volume and/or capability for an operator to continue operations in the event the chromatograph goes off-line or requires maintenance. Although the loop does not provide for confirmation when used alone, by relying on flow measurements, the presence of the flow control loop permits continuation of the refined gas blending at the operator's discretion. Such an embodiment includes flow transmitters 54, such as ROSEMOUNT Model 30515FP Integral Orifice Transmitter, disposed in-line between the control unit 32 and, respectively, the biogas feedstock conduit 22 and refined gas conduit 38. The flow transmitters 54 sense the respective flow rates of the biogas feedstock stream conduit 22 and, if actuated, the refined gas conduit 36. A displayed flow ratio indicates an estimated but non-confirmed BTU level/energy content of the blended output stream. When combined with analysis by a chromatograph, the flow rates detected by the flow transmitters 54 can be used for calculating adjustments to flow through the actuatable valve 36.

It should be understood by those skilled in the art that other modifications and embodiments of the invention will come to mind to which the invention pertains, having benefit of the teaching presented in the foregoing description and associated drawings. It is therefore understood that the invention is not limited to the specific embodiments disclosed herein, and that many modifications and other embodiments of the invention are intended to be included within the scope of the invention. Moreover, although specific terms are employed herein, they are used only in generic and descriptive sense, and not for the purposes of limiting the description of the invention.

What is claimed is:

1. A gas blending system comprising:
a biogas feedstock source providing a biogas feedstock stream having a first energy content;
a first sample take-off probe for sample take-off from said biogas feedstock stream for energy content analysis;
an analyzer for energy content analysis and generating data signals representative thereof;
a control unit for receiving said energy content analysis data signal and transmitting a control signal responsive thereto;
a refined gas source in selective fluid communication with said biogas feedstock stream and disposed downstream of said first sample take-off probe, the refined gas source selectively providing a refined gas having a known energy content exceeding that first energy content;
a valve in signal communication with said control unit responding to the transmitted signal, said valve for controlling refined gas flow from said refined gas source, said valve being actuatable between a first open position and a second closed position, where said valve when in said first open position selectively introduces said refined gas into the biogas feedstock stream to generate a blended biogas stream upon detection of said first energy content falling below a preset minimum;
a second sample take-off probe for sample take-off from said blended biogas stream, said second take-off probe being disposed downstream of said refined gas input source, for energy content analysis and energy content verification of said blended biogas stream as meeting or exceeding said preset minimum; and
an output of said blended biogas stream.

2. The system of claim 1 where said valve is an electrically actuated solenoid valve which is in electronic signal communication with said control unit to regulate a flow of refined gas introduced to said biogas stream.

3. The system of claim 2 where the sample take-off from the biogas feedstock stream is continuous.

4. The system of claim 2 where the sample take-off from the biogas feedstock stream is periodic.

5. The system of claim 2 further comprising a first flow rate sensor associated with the biogas feedstock stream, said flow rate sensor for detecting and generating a signal representative of the biogas feedstock stream flow rate where said flow rate sensor is in signal communication with said control unit.

6. The system of claim 5 further comprising a second flow rate sensor associated with said refined gas source, said second flow rate sensor in signal communication with said control unit for detecting and generating a signal representative of the refined gas flow rate.

7. The system according to claim 6 further comprising a system interface having a processor, a screen, and an input device, the system interface being in signal communication with the control unit for transmitting control signals to, and receiving system data from, the control unit.

8. The system of claim 1 where the sample take-off from the blended biogas is periodic.

9. The system of claim 1 further comprising a refined gas impingement tube for promoting enhanced uniformity of blended biogas.

10. The system of claim 9 where the impingement tube comprises an elongated cylinder with an axial bore and spaced, radially oriented refined gas ports for injection of refined gas over a substantial cross-section of the biogas feedstock stream.

11. The system of claim 9 where the blended and unblended biogas samples are communicated to the analyzer from the respective sample takeoff probes using heat traced tubing.

12. The system of claim 1 where the analyzer is a dual stream gas chromatograph.

13. The system of claim 1 further comprising a sample take-off distribution panel.

14. The system of claim 1 further comprising a first sample conditioner disposed between, and in fluid communication with, the sample takeoff probe and the analyzer to maintain vapor phase stability of the sample extracted from the biogas feedstock stream.

15. The system of claim 14 further comprising a second sample conditioner associated with the second take-off probe.

16. A method of blending a biogas feedstock stream from a first source having a first energy content with a refined gas from a second refined gas source having a known energy content higher than the first energy content to provide a blended biogas having a third energy content in a select range using a gas blending system including a system interface and a control unit in signal communication with an actuatable valve disposed in a flow path of a refined gas from a refined gas source, comprising the steps of:
 a) extracting a sample from the biogas feedstock stream;
 b) conditioning the extracted sample for analysis by an energy content analyzer and generating data corresponding to the biogas feedstock stream energy content;
 c) determining if the biogas stream possesses an energy content less than a pre-established minimum;
 d) generating a control signal by the control unit when the first energy content is detected to fall below the pre-established minimum and communicating the control signal to said actuatable valve for injection of a refined gas into the biogas feedstock stream to form the blended biogas;
 e) extracting a sample of the blended biogas and analyzing the energy content thereof to verify the third energy content exceeds the pre-established minimum; and outputting the blended biogas.

17. The method of claim 16 further comprising the steps of sensing the flow rate of the biogas feedstock stream and the flow rate of the refined gas injected into the biogas feedstock stream and generating a flow rate ratio based on the sensed respective flow rates.

* * * * *